United States Patent

Pan et al.

Patent Number: 5,262,546
Date of Patent: Nov. 16, 1993

[54] PROCESS FOR THE PREPARATION OF 5,6-DIACETOXYINDOLE

[75] Inventors: Yuh-Goo Pan, Stamford; Mu-Ill Lim, Trumbell, both of Conn.

[73] Assignee: Clairol, Inc., New York, N.Y.

[21] Appl. No.: 977,370

[22] Filed: Nov. 17, 1992

[51] Int. Cl.$^5$ .................................. C07D 209/08
[52] U.S. Cl. ........................................ 548/508
[58] Field of Search .......................... 548/508

[56] References Cited

U.S. PATENT DOCUMENTS 3,732,245  5/1973  Batcho et al. .................. 548/508

Primary Examiner—Mary C. Lee
Assistant Examiner—Jacqueline Haley
Attorney, Agent, or Firm—Morton S. Simon

[57] ABSTRACT

An indole of the formula

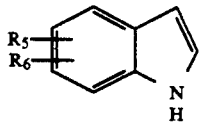

wherein $R_5$ and $R_6$ are acetoxy or hydrogen, at least one of $R_5$ and $R_6$ being acetoxy, is prepared, in good yield, in a one pot synthesis, without extraction, recrystallization or isolation of intermediate reaction product; A compound of the formula

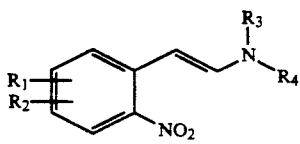

wherein $R_1$ and $R_2$ are benzyloxy or hydrogen, provided that at least one of $R_1$ and $R_2$ is benzyloxy, is subjected to reductive cyclization followed by acetylation of the resultant reaction product.

5 Claims, No Drawings

PROCESS FOR THE PREPARATION OF 5,6-DIACETOXYINDOLE

FIELD OF INVENTION

The present invention provides a less expensive method for the production of 5,6-diacetoxyindole ("DAI") from trans-4,5-dibenzyloxy-β-pyrrolidino-2-nitrostyrene. In the present method the three step transformation, which includes reductive cyclization, debenzylation and acetylation, is carried out in one reaction vessel with no intermediate isolation or purification steps. Consequently, the present method is henceforth referred to as a "one pot" method.

BACKGROUND OF THE INVENTION

DAI is a known hair dye. It is an expensive material because all prior art syntheses of same involve difficult multi-step procedures, usually involving from 5 to 8 steps. Moreover, extensive purification is required in order to isolate a good quality DAI. Because of the high expense the aforementioned prior art syntheses have not proven suitable from an industrial standpoint.

R. J. S. Beer, et al (J.Chem.Soc.223,1948) teach production of DAI by reductive cyclization of 4,5-diacetoxy-2,β-dinitrostyrene with Fe in acetic acid. 10 g of Fe, 40 ml of acetic acid and 50 ml of absolute alcohol were required for reduction of 2 g of 4,5-diacetoxy-2,β-dinitrostyrene. Moreover, in order to isolate DAI from the reaction mixture, several extractions with ether (at least 5 times), and recrystallization, were necessary.

B. P. Murphy (J.Org.Chem.,50,5873, 1983) teaches that DAI may also be obtained by reductive cyclization of 4,5-diacetoxy-2,β-dinitrostyrene with 5% Pt/C, in acetic acid, followed by acetylation. The process required 5 operations. Moreover, it was necessary to use HPLC to purify DAI so produced.

In U.S. Pat. No. 3,732,245, issued May 8, 1973, Batcho et al disclose a process and intermediates for the preparation of indoles from ortho-nitrotoluenes. The process comprises condensing an ortho-nitrotoluene with formamide acetal then treating the reaction product with a reducing agent to yield the indole. At column 4 patentees indicate that their invention involves condensing the methyl function of an ortho-nitrotoluene with the formyl group of a formamide acetal to produce a nitrobenzene derivative bearing a N,N-disubstituted aminovinyl function ortho to the nitro group. The nitro group is reduced to an amino group which concurrently displaces the N,N-disubstituted amino function and effects cyclization to a compound having an indole nucleus.

The synthesis described by Batcho et al is a multi-step process. The final product, 5,6-dibenzyloxyindole, was purified by a silica gel column chromatography followed by recrystallization. Although the patent does not suggest or indicate the synthesis of DAI by this route, one can visualize that DAI can be obtained from 5,6-dibenzyloxyindole by a two-step procedure, debenzylation and subsequent acetylation.

SUMMARY OF THE INVENTION

There is a clear need for a simpler and less costly process for producing DAI. The present invention provides such a process.

The pivotal step in the synthesis of DAI is the final reductive cyclization and isolation of DAI. As is evident from the aforementioned processes, the isolation is time consuming, difficult and expensive. The process of the present invention permits one to isolate DAI directly from the reaction mixture in a one pot process. Extraction, recrystallization or HPLC isolation of the intermediate product is not required.

In addition, despite the fact that standard reductive cyclization (10% Pd/C, EtOAc-CH₃COOH-EtOH) of trans-4,5-diacetoxy-2,β-dinitrostyrene gives a variety of side products, the one-pot procedure involving standard reductive cyclization, to our surprise, gives a good yield of DAI with high quality.

Reductive cyclization of trans-4,5-dibenzyloxy-β-pyrrolidino-2-nitrostyrene to 5,6-dibenzyloxyindole is generally known to proceed sequentially in accordance with the following general reaction scheme:

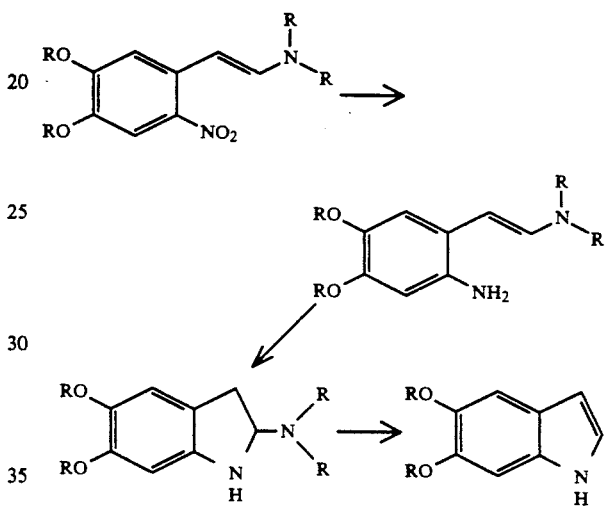

Because several intermediates are involved during reductive cyclization, the yield varies depending on the reaction conditions. The formation of a variety of side products is expected. This is a common feature of this methodology. Moreover, such side products are oxidized when exposed to air whereby a tarry material results. Consequently, it is necessary to first purify indoles containing electron-donating substituents before they are further reacted.

Further complication might occur because reduction of the nitro group to the amino group proceeds in three steps as follows:

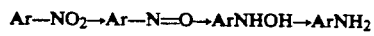

Hydroxyamine derivative (Ar—NHOH) can undergo an intramolecular cyclization to produce an N-hydroxyindole derivative. Another expected complication is that the reaction conditions (Pd-C, hydrogen) employed in the reductive cyclization are known to cleave the benzyl group. One skilled in the art would therefore expect that the reductive cyclization would result in debenzylation occurring during and after cyclization. Thus, after acetylation, the skilled chemist would expect the reaction to yield a complex mixture of reaction products whereby isolation of DAI would be made very difficult. Indeed as shown in Example 3 of the present application, attempted isolation of 5,6-dihydroxyindole after the hydrogenation of trans-4,5-dibenzyloxy-β-pyrrolidino-2-nitrostyrene was found to be very difficult. During solvent removal, 5,6-dihydroxyindole was rapidly oxidized. This unexpected result was due to the several above-mentioned by-products.

In contrast, under similar conditions, 5,6-dibenzyloxyindole was deprotected to the corresponding 5,6-dihydroxyindole, in excellent yield.

It was indeed surprising and unexpected that the one-pot process of the present invention enables direct isolation of DAI from water in a very good yield (65%) and without any purification step.

DETAILED DESCRIPTION OF THE INVENTION

The process of the present invention is illustrated as follows:

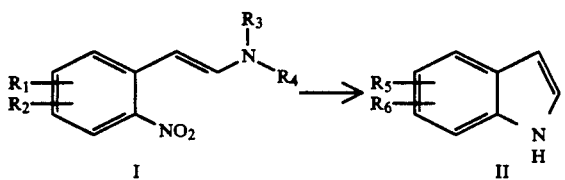

In the general formula I depicted above, one of $R_1$ and $R_2$ is benzyloxy and the other is hydrogen or $R_1$ and $R_2$ are both benzyloxy; and $R_3$ and $R_4$ are, independently, lower alkyl ($C_1$ to $C_6$) or $NR_3R_4$ is pyrrole, pyrrolidine, piperidine or morpholine.

In the general formula II above, $R_5$ and $R_6$ are, independently, acetoxy or hydrogen, provided that at least one of $R_5$ and $R_6$ is acetoxy.

The compounds of formula I are reduced by catalytic hydrogenation or catalytic transfer hydrogenation followed by acetylation to produce the corresponding indoles of formula II. The catalytic hydrogenation may be effected in any conventional manner so long as the process employed enables cleavage of the benzyl groups. Preferably, the process is carried out at a temperature in the range of room temperature to 100° C. and under a hydrogen pressure of from atmospheric pressure to 60 psi. Any suitable hydrogenation catalyst such as palladium or platinum may be employed. The preferred catalyst is palladium which is supported on carbon and preferably containing 3 to 10% palladium.

For the catalytic transfer hydrogenation reviewed by R. A. W. Johnstone and A. H. Wilby (Chem.-Rev.1985,85,129–170), hydrogen donors are hydrazine, formic acid, formate, phosphinic acid, phosphinate, indoline, cyclohexene, and cyclohexadiene. The preferred catalyst is palladium on carbon containing 3 to 10% palladium.

After the reduction is complete the reaction product is subjected to acetylation with acetic anhyride or acetyl chloride in the presence of an organic base such as triethylamine, pyridine, 4-dimethylaminopyridine or a mixture thereof. Acetylation yields the mono-acetoxy ($R_5$=OAc, $R_6$=H) or diacetoxy ($R_5$=$R_6$=OAc) compound.

When the acetylation is complete, the catalyst is removed and the filtrate is concentrated. The products can be isolated by adding cold water or ice. Easy isolation constitutes another advantage of the one pot process of the present invention.

The improved method of the present invention is illustrated in the following Examples:

EXAMPLE 1

Synthesis of 5,6-diacetoxyindole

A suspension of 17.2 g of trans-4,5-dibenzyloxy-β-pyrrolidino-2-nitrostyrene (prepared from 3,4-dihydroxytoluene by a modified procedure of U.S. Pat. No. 3,732,245) and 3.4 g of 10% Pd/C catalyst in 200 ml ethyl acetate was shaken at room temperature, under hydrogen atmosphere and at 50 psi, for 5 hours. To this reaction mixture was added a solution of ethyl acetate (100 ml) containing acetic anhydride (24 ml), triethylamine (20 ml) and dimethylaminopyridine (800 mg) which was previously saturated with hydrogen. The resultant mixture was stirred for 30 minutes at room temperature. The catalyst was removed over a layer of Celite and the filtrate was evaporated to give an oily residue to which crushed ice was added. The resulting white precipitate was collected by filtration to give 6.08 g (65%) of DAI: mp 130°–131° C.; HNMR (300 MHz, DMSO-d6)δ 2.24 (s,6H), 6.42 (s,1H), 7.22 (s,1H), 7.32 (s,1H), 7.39 (m, 1H) 11.22 (s,1H).

EXAMPLE 2

Synthesis of 4-acetoxyindole

A suspension of 3.24 g of trans-6-benzyloxy-2-nitro-β-pyrrolindino -styrene (prepared from 2-methyl-3-nitrophenol by a procedure reported in Organic Synthesis, Coll. Vol. 7, 34, 1990) and 648 mg of 10% pd/C catalyst in 20 ml of ethyl acetate was shaken under hydrogen atmosphere and at 50 psi, for 5 hours. To this reaction mixture were added acetic anhydride (1.4 ml), triethylamine (2.1 ml) and dimethylaminopyridine (324 mg). The resultant mixture was stirred for 1 hour at room temperature. The catalyst was removed over a layer of Celite and the filtrate was evaporated under reduced pressure to give an oily residue to which crushed ice was added. The resulting white precipitate was collected by filtration to give 1.2 g (69% yield) of 4-acetoxyindole: mp 97°–98° C.; HNMR (300 MHz, DMSO-d6)δ 2.32 (s,3H), 6.31 (s,1H), 6.71 (d,1H,J=8Hz), 7.05 (t,1H, J=8 Hz), 7.28 (d,1H,J=8Hz), 7.32 (s,1H), 11.27 (s,1H).

EXAMPLE 3

Attempted Synthesis of 5,6-Dihydroxyindole from Trans-4,5-Dibenzyloxy-β-Pyrrolindino-2-Nitrostyrene Trans-4,5-dibenzyloxy-β-pyrrolidino-2-nitrostyrene (2.2 g, 5 mmol) and 200 mg of 10% Pd/C in 20 ml of ethanol were hydrogenated (1 atm, room temperature). The progress of the reaction was monitored by tlc (silica gel CHCl3/CH3OH=9/1). After 4 hours the only product detected by spraying the tlc plate with Erlich reagent was 5,6-dihydroxyindole.

The catalyst was removed under an nitrogen atmosphere (glove bag) and the solvent was evaporated in vacuo. However, 5,6-dihydroxyindole was rapidly polymerized under these conditions.

EXAMPLE 4

Synthesis of 5-Acetoxyindole

The one pot process of Example 1 is followed except that the starting material is trans-5-benzyloxy-β-pyrrolidino-2-nitrostyrene. 5-acetoxyindole is thereby prepared in good yield.

EXAMPLE 5

Synthesis of 6-Acetoxyindole

The one pot process of Example 1 is followed except that the starting material is trans-4-benzyloxy-β-pyrrolidino-2-nitrostyrene. 6-acetoxyindole is thereby prepared in good yield.

EXAMPLE 6

Synthesis of 5-Acetoxy-6-Methylindole

The one pot process of Example 1 is followed except that the starting material is trans-5-benzyloxy-4-methyl-β-pyrrolidino-2-nitrostyrene. 5-acetoxy-6-methylindole is thereby prepared in good yield.

What is claimed is:

1. A process for preparing a mono-or diacetoxyindole of the formula

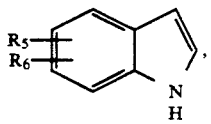

wherein $R_5$ and $R_6$ are, independently, acetoxy or hydrogen, provided that at least one of $R_5$ and $R_6$ is acetoxy, comprising (i) subjecting a compound of the formula I

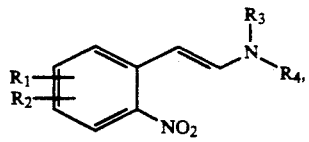

wherein $R_1$ and $R_2$ are, independently, benzyloxy or hydrogen, provided that at least one of $R_1$ and $R_2$ is benzyloxy, and $R_3$ and $R_4$ are, independently, lower alkyl($C_1$-$C_6$) or $NR_3R_4$ is pyrrole, pyrrolidine, piperidine or morpholine, to reductive cyclization to produce a reaction product; and (ii) acetylating said reaction product to produce the indole of formula II; steps (i) and (ii) being carried out in one pot with no extraction, recrystallization or isolation of said reaction product.

2. The process according to claim 1, wherein the reductive cyclization is effected by catalytic hydrogenation utilizing hydrogen and Pd/C or Pt/C.

3. The process according to claim 2, wherein the acetylation step (ii) is effected by further reacting said reaction product with acetic anhydride or acetyl chloride and an organic base selected from the group consisting of triethylamine, pyridine, 4-dimethylaminopyridine and a mixture thereof.

4. The process according to claim 3, further including the step of (iii) recovering the indole of formula II.

5. The process according to claim 4, wherein the indole of formula II is recovered by filtering off the catalyst, concentrating the filtered reaction mixture, then adding cold water or ice to the filtered reaction mixture and recovering the indole of formula II.

* * * * *